United States Patent
Stoll

(10) Patent No.: US 8,753,278 B2
(45) Date of Patent: Jun. 17, 2014

(54) PRESSURE CONTROL IN MEDICAL DIAGNOSTIC ULTRASOUND IMAGING

(75) Inventor: Jeffrey Stoll, San Mateo, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 355 days.

(21) Appl. No.: 12/895,616

(22) Filed: Sep. 30, 2010

(65) Prior Publication Data

US 2012/0083692 A1    Apr. 5, 2012

(51) Int. Cl.
*A61B 8/00*    (2006.01)

(52) U.S. Cl.
USPC ........................................................ 600/438

(58) Field of Classification Search
USPC ........................................................ 600/437
See application file for complete search history.

(56) References Cited

U.S. PATENT DOCUMENTS

| | | | |
|---|---|---|---|
| 6,425,865 B1 | 7/2002 | Salcudean et al. | |
| 6,511,427 B1 | 1/2003 | Sliwa, Jr. et al. | |
| 6,876,879 B2 | 4/2005 | Dines et al. | |
| 2004/0254460 A1 | 12/2004 | Burcher et al. | |
| 2006/0173320 A1 | 8/2006 | Radulescu | |
| 2006/0193437 A1* | 8/2006 | Boeing et al. | 378/115 |
| 2007/0073145 A1 | 3/2007 | Fan et al. | |
| 2008/0021317 A1 | 1/2008 | Sumanaweera | |
| 2008/0269605 A1* | 10/2008 | Nakaya | 600/437 |

* cited by examiner

*Primary Examiner* — Jonathan Cwern

(57) ABSTRACT

Contact pressure from a transducer is controlled in medical diagnostic ultrasound imaging. Rather than measuring pressure directly using a pressure sensor on the transducer, the compression of tissue within the patient may be measured using ultrasound scanning. The desired amount of compression in the region of interest for diagnosis may be obtained. For example in breast imaging, the desired compression for imaging a portion of the breast is compared to compression measured from ultrasound data. Once the desired tissue compression is achieved, the pressure applied by the transducer is maintained while the diagnosis scan occurs. For example, a robotic arm locks or otherwise maintains the pressure during scanning.

18 Claims, 2 Drawing Sheets

PRESSURE CONTROL IN MEDICAL DIAGNOSTIC ULTRASOUND IMAGING

BACKGROUND

The present embodiments relate to medical diagnostic ultrasound imaging. In particular, pressure control of the transducer against the patient is provided.

In ultrasound imaging, the user places a transducer against the patient. For good acoustic coupling, the user presses the transducer towards the patient. If there is too little compression, the acoustic coupling may be insufficient. Too much pressure may cause patient or sonographer discomfort and may adversely distort tissue. The amount of contact force to apply is a subject of user training, requiring numerous scans to achieve proficiency.

Image artifacts may result from incorrect pressure. For example, a patient's breast is to be scanned in three dimensions with ultrasound using a scanning pod. Over-compression of the breast by the scanning pod or transducer may lead to two related compression artifacts. The first artifact is a reduction in anatomic resolution caused by compression of small tissue structures. The physical separation and/or impedance contrast between adjacent structures cannot be resolved in the ultrasound image if the pressure causes the tissue boundaries to be very close together. This loss of information results in a loss of diagnostic yield and a loss of confidence for detecting small pre-cancerous or neo-cancerous lesion detection.

The second artifact is a reduction in anatomic resolution due to blurring of tissue over small regions. The transducer may be moved to scan different planes for three-dimensional imaging. As the transducer moves laterally, friction between the transducer face and the tissue causes lateral displacement of the tissue and an increase in static shear force. When this shear force reaches a certain threshold—defined by properties including the contact normal force, tissue stiffness, tissue shape and contact lubrication—the contact begins to slip, leading to a relaxation of the tissue counter to the transducer movement. Following some relaxation of the tissue, the contact sticks again and the process repeats. This is referred to as "stick-slip." The result within an image of a volume is a blurring of image detail corresponding to locations scanned during tissue relaxation.

BRIEF SUMMARY

By way of introduction, the preferred embodiments described below include methods, instructions and systems for controlling transducer contact pressure in medical diagnostic ultrasound imaging. Rather than measuring pressure directly using a pressure sensor on the transducer, the compression of body tissues within the patient due to transducer pressure may be measured using ultrasound scanning. For example in breast imaging, the desired compression for imaging a portion of the breast is compared to compression measured from ultrasound data. Once the desired compression is achieved, the pressure applied by the transducer is maintained while the diagnosis scan occurs. For example, a robotic arm locks or otherwise maintains the pressure during scanning.

In a first aspect, a method is provided for controlling transducer contact pressure in medical diagnostic ultrasound imaging. An ultrasound transducer is placed against a patient's breast. An amount of pressure applied by the ultrasound transducer against the breast is increased or decreased. The ultrasound transducer is used to ultrasonically scan a region of the breast while increasing or decreasing the transducer contact pressure. Body tissue compression caused by the transducer contact pressure is measured with ultrasound data received by the transducer due to the scanning. The transducer contact pressure is controlled as a function of the measured body tissue compression such that the contact pressure stabilizes at a desired level.

In a second aspect, a non-transitory computer readable storage medium has stored therein data representing instructions executable by a programmed processor for controlling transducer contact pressure in medical diagnostic ultrasound imaging. The storage medium includes instructions for measuring body tissue compression caused by an ultrasound transducer with ultrasound data from an ultrasound scan, regulating an amount of the pressure applied by the transducer as a function of body tissue compression, and scanning with the ultrasound transducer.

In a third aspect, a system is provided for controlling pressure in medical diagnostic ultrasound imaging. A support arm operable to hold a transducer. An ultrasound imaging apparatus connects with the transducer. The ultrasound imaging apparatus is configured to acquire, with the transducer, ultrasound data representing a patient. A processor is configured to determine an amount of contact force applied by the transducer against a patient. The processor determines the amount from the ultrasound data. The processor is configured to determine when the amount is sufficient.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Figure 1:
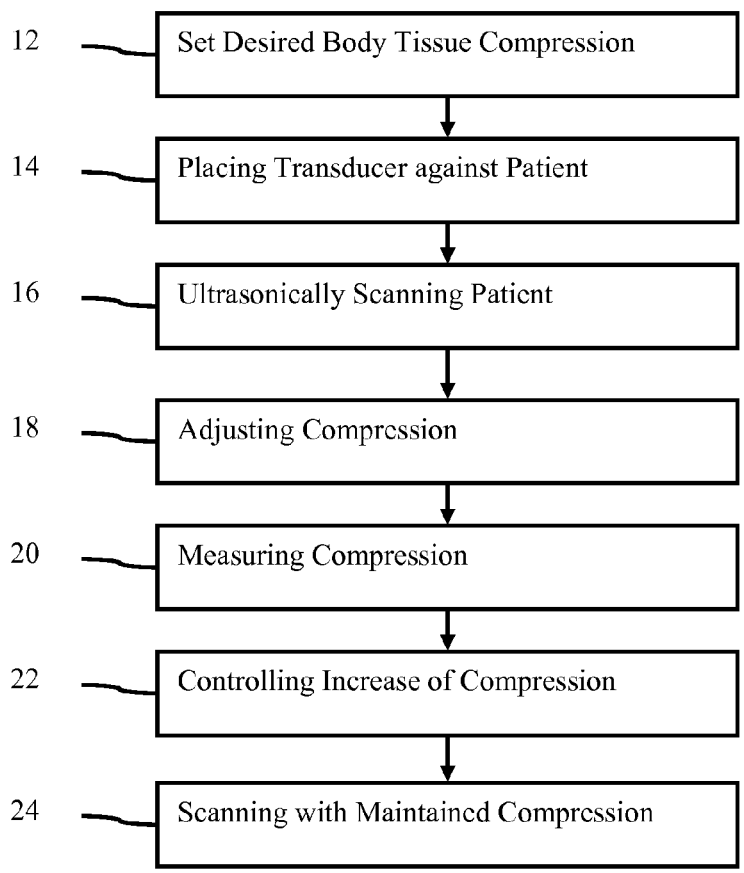
FIG. 1 is a flow chart diagram of one embodiment of a method for controlling pressure in medical diagnostic ultrasound imaging.

The contact pressure of an ultrasound transducer is regulated to maximize diagnostic yield within a region of interest. By controlling transducer contact pressure, imaging artifacts may be minimized. Some minimal contact pressure is required to transmit and receive sound waves through body tissue. An optimal contact force may be defined as that which produces minimal compression within a region of interest while providing sufficient contact to obtain diagnostic images. The optimal force may vary based on the patient and region of interest within the body. The optimal transducer contact pressure may be calculated based on measured physiologic parameters including but not limited to patient biometric data (height, weight, age, etc.). Transducer contact pressure is controlled by automatically regulating contact pressure about a desired level, limiting contact pressure to not exceed a threshold, or indicating to a user when sufficient force has been applied.

It has been observed in some cases that proper transducer contact pressure may be determined through monitoring the compression of superficial layers of body tissue (i.e. skin layers). When the separation of certain skin layers is reduced just to the point where they can no longer be distinguished, the contact pressure is appropriate for scanning deeper regions of body tissue. Extending this observation, applying automatic image analysis of tissue deformation toward determining optimal transducer contact pressure may minimize training requirements for ultrasound imaging and reduce inter-operator ultrasound scan variability. The desired transducer contact pressure to apply is determined from measurements derived from medical images or other type of scan data. For example, the transducer contact pressure is controlled based on measured tissue deformation and/or detection of reduced blood flow or increased blood velocity. The actual transducer contact pressure is then compared to the desired transducer contact pressure.

In one example embodiment, the measurement and control of the contact pressure applied by the transducer is used in an automated breast scanner. The breast scanner is supported by a robotic arm. The robot or the user positions the scanner against a patient's breast. The user or robot applies increasing pressure against the breast. The resulting compression of body tissue is measured as pressure is increased. The pressure increases until a desired compression of body tissue is obtained. Once the desired pressure is obtained, the transducer in the scanner moves mechanically to scan different planes while the pressure is maintained. Three-dimensional data is provided for diagnosis. The data may have fewer artifacts as the pressure may be minimal enough to avoid at least some stick-slip and over compression while being sufficient to allow for scanning contact over a desired lateral extent of the breast.

The techniques described herein may be used in automated or non-automated systems. The techniques described herein may be used for breast scanning or scanning of other parts of a patient.

FIG. 1 shows a method for controlling transducer contact pressure in medical diagnostic ultrasound imaging. Additional, different or fewer acts may be provided. For example, act 24 is not provided. Instead, the scanning of act 16 is also used for diagnosis. The acts are performed in the order described or shown, but other orders may be provided. For example, act 18 starts before starting act 16.

In act 12, a desired transducer contact pressure is set. The desired transducer contact pressure may be represented by a threshold value. The desired pressure may be a value for transducer contact pressure or a value indicative of this pressure. For example, the desired value is an amount of compression, a distribution of compression, an amount of flow due to change in diameter, a change in diameter, a change in thickness, or any other type of value reflective of the pressure. The transducer contact pressure may cause various effects on the tissue and/or fluids. The desired pressure is a desired value for a measurement of one or more of these effects of the pressure regardless of whether the actual pressure is determined. The desired transducer contact pressure indicates an amount of body tissue compression.

The desired value is set as a predetermined value. For example, experimental use may indicate the desired value. As another example, a model may indicate the desired value. The value is predetermined by the manufacturer, programmer, or a user. For example, a user selects a value to be used for a given examination, a given patient, a given imaging apparatus, a clinic, a hospital or other group.

In one embodiment, the desired value is determined adaptively. The desired value is set by the user as input or set using automated measurement. The desired value adapts to different patients or environmental considerations. In one embodiment, the desired value is determined adaptively based on a physiological characteristic of the patient. The desired value for body tissue compression may be based on a metric involving the geometry of compression throughout the tissue or within a region of interest and the quality of transducer contact for imaging. Example physiological characteristics include age, height, weight, cup size, body mass index, or combinations thereof. Any characteristic directly or indirectly affecting the tissue elasticity, stiffness, or quality affecting the stick-slip or ability to conform to the array for contact may be input. The user inputs or a processor determines one or more characteristics, and a processor applies a model to determine the desired value based on the characteristics.

Figure 2:
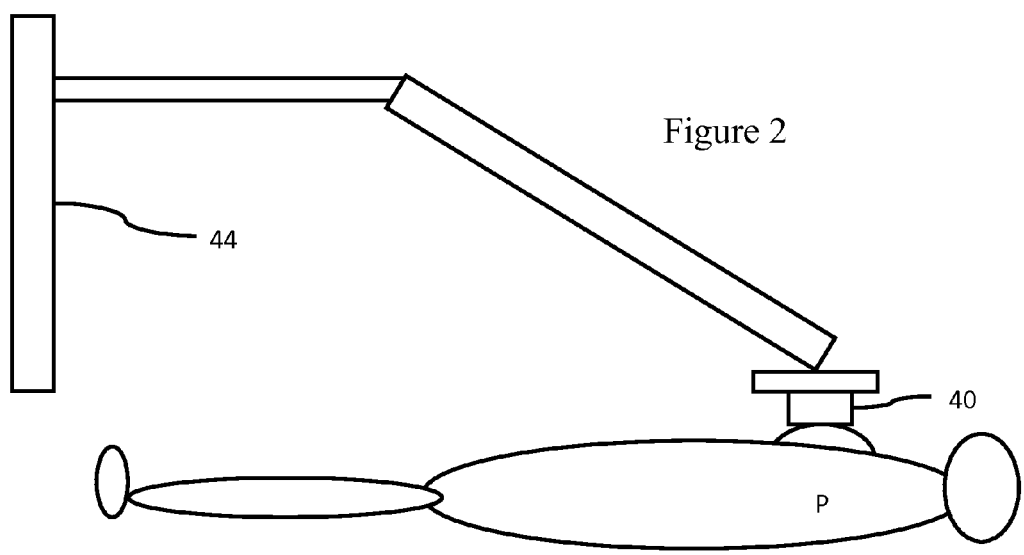
FIG. 2 is an example illustration of a support arm used to maintain pressure during ultrasound scanning.

In act 14, an ultrasound transducer is placed against a patient's breast. The user positions the transducer by hand. For example, the user places a handheld probe on the patient. Alternatively, a robot positions the transducer without or pursuant to user guidance. The transducer is placed in contact with the skin of the patient. FIG. 2 shows the transducer 40 being placed against a patient P while the transducer 40 is held by a support arm 44. In other embodiments, the transducer is placed at a desired location within the patient, such as when using an intra-operative probe.

The transducer placement is maintained. Either the user or the robotic support maintains the position of the transducer. As the transducer contact pressure on the patient is increased by the user or robotic movement, transducer placement is adjusted within the spatial plane defined by the ultrasound image and is otherwise maintained. For example, the user presses the transducer, held by a support arm, against the patient. Once the user releases the pressing, the robotic support may maintain the transducer in position until a release command or application of additional force away from the patient occurs.

In act 16, the patient is scanned. The transducer transmits ultrasound energy into the patient and receives echoes. The transducer converts the echoes to electrical signals, which are used to generate information representing the scanned region of the patient. In one example, the breast of a patient is scanned. A sub-set of the breast may be scanned, such as along a line extending from the transducer into the breast or a line at any arbitrary location (e.g., C-scan). With a moveable transducer, the center of the breast or other locations is scanned in act 16. The region may be a planar region, such as a rectangular, sector, or Vector® region extending from the transducer into the breast. A volume region may be scanned.

The ultrasound scanning may be repeated. The first scan occurs after placement of the transducer against the patient or region to be scanned in act 14. The first scan occurs before increasing the pressure in act 18, but may occur after the pressure begins to increase in act 18. The scanning is repeated as the pressure and resulting compression increase in act 18. As a result, ultrasound information for the region is acquired while the region is subjected to different physical or non-ultrasound pressures from the transducer.

The acquired ultrasound information is B-mode data, flow data (e.g., velocity, variance, or energy), harmonic mode data, spectral Doppler data (e.g., continuous wave Doppler), or other type of data. In one embodiment, the ultrasound information is flow data for showing the velocity or change in velocity over time at one or more locations. In another embodiment, the ultrasound information is B-mode data for showing a tissue layer thickness (e.g., skin layer), vessel dimension, or speckle locations in a region.

In another embodiment, the ultrasound information is B-mode or other data for estimating tissue stiffness or elasticity. Elasticity data is information estimating stiffness of tissue, such as strain. The data is responsive to compression force or other stress applied to the tissue being scanned. For example, a transducer applies pressure axially while being maintained at a lateral location. Ultrasound scanning is performed while applying axial pressure with the transducer against the patient. Alternatively, another source of stress or compression is used, such as acoustic energy or movement within the body.

In act 18, the contact pressure applied by the transducer is increased. The user and/or the robotic support arm increase the pressure. The pressure increases axially and/or laterally. The pressure increase causes greater compression of the tissue. The greater compression may be more or less in different regions, depending on the direction and tissue properties. The pressure increase may be linear or non-linear with time and may occur at any rate. The pressure starts at zero or some other pressure and increases until sufficient pressure is reached or the patient begins to experience pain or discomfort.

While the pressure is increasing in act 18, acts 16 and 20 are performed one or more times. For example, acts 16 and 20 are performed multiple times to allow tracking or detection of the compression caused by the increasing pressure.

In act 20, the compression of body tissue caused by the transducer contact pressure is measured. The effects of pressure applied by the ultrasound transducer are measured using any one or more parameters. Flow, flow rate, thickness, distance, area, volume, existence of an object, elasticity, strain, strain rate, or other characteristic is measured. The compression or pressure may be directly or indirectly measured. The measured parameter may be used without further processing. Alternatively, the measured parameter is used with a model to determine a value for a compression or pressure parameter.

The measurement is performed with ultrasound data. Data received by the transducer due to the scanning of act 16 is used, at least in part, to measure the parameter. Any type of ultrasound scan is used, such as B-mode, M-mode, spectral Doppler, flow mode (velocity, energy, and/or variance), harmonic mode, or contrast agent imaging mode. The detected or pre-detection ultrasound data is used to measure pressure.

The measurement is performed for one or more locations within the patient. A region of interest for diagnosis may be indicated by the user or determined by the processor. The compression may be measured in the region of interest. Full or sparse sampling for measurement may be provided in the region of interest for diagnosis. Measuring in the region of interest allows more direct control of the desired amount of compression of the tissue to be examined. Alternatively, one or more locations outside the diagnosis region of interest are used. For example, the measurement in made in a region more in the near field than used for diagnosis. For example, the measurement is of the skin layer or layers. Combinations of within and outside of the diagnosis region of interest may be used.

Where multiple measurements are made, such as at different locations or using different parameters, the measurements may be combined. For example, an average is determined. The combination may be weighted, such as weighting measured values in the diagnosis region of interest more heavily. As another example, the measurements are combined in a determination of distribution. The rate of change or difference between locations is determined. The distribution of the pressure compression field may be used.

In one embodiment, tissue deformation is measured. For example, a two-dimensional B-mode or harmonic mode scan is analyzed in the near field. The skin layer is identified by the user or the processor. The thickness of the skin layer is a measure of tissue deformation indicating compression or pressure. Alternatively, the image may be analyzed to determine a number of skin layers or whether a particular skin layer is visible or detectable. If not visible or detectable, sufficient compression is provided in this binary measurement.

The amount of body tissue compression may be directly measured. The tissue deformation caused by the pressure is measured with speckle tracking. The speckle from frames or lines of ultrasound data obtained in act 16 by scanning at different times is correlated. Any correlation may be used, such as cross-correlation, minimum sum of absolute differences, or other similarity measure. Since the data is from the same tissue region, but subjected to different amounts of deformation, the correlation may be used to determine an offset in the axial or other direction caused by the transducer contact pressure. One, two, or three dimensional offset with or without one, two, or three degrees of rotational offset may be determined. The relative spatial position of the two frames or lines of data associated with highest correlation provides the offset.

The radio frequency data or pre-detected data is used to determine the alignment. Pre-detected data may provide more accurate information for the motion vector between frames of data. Any now known or later developed technique for estimating the motion vector or determining the displacement between frames or data may be used. B-mode or other detected data may be used in other embodiments.

In another approach using speckle tracking, compression or elastography algorithms are used to detect integrated displacement and/or local compression. Compression is calculated from the deformation field. This is obtained by measuring tissue deformation under load. Since speckle tends to decorrelate quickly, single points may not be tracked throughout all frames. Instead, frame-to-frame correlation indicates an Eulerian deformation velocity within the body tissue. This deformation velocity is integrated over several frames in order to arrive at a final estimate of the deformation field, from which body tissue compression may be derived.

In yet another approach, body tissue compression is determined by measuring a diameter of one or more vessels. The user indicates vessel walls from B-mode or harmonic mode images. Alternatively, the vessel walls are determined as the outer extent of flow mode data. An automated boundary or vessel detection algorithm may be used. The difference in diameter or other spatial measure of the vessel (e.g., volume, radius, circumference, or position relative to other structures) indicates a change in compression of the surrounding body tissue.

In one embodiment, the variation or change in flow is used to determine the transducer contact pressure. The restriction of flow area within a vessel due to body tissue compression may cause an increase in flow velocity. Velocity at a given location in the vessel (e.g., center of the vessel) is measured using flow velocity (e.g., PW flow mode) or spectral Doppler (e.g., CW flow mode). The velocity may be measured for a location within the flow (e.g., maximum velocity location) or an area across the vessel (e.g., average or total flow velocity). Power or energy Doppler data may be used in other embodiments. As an alternative to an increase in flow velocity, constriction of vessel walls may reduce the amount of flow. Change in flow volume rate or other measure of overall flow may indicate a change in body tissue compression.

In act 22, body tissue compression is controlled. An amount of contact pressure applied by the transducer is regulated as a function of the measured pressure. The measured body tissue compression is used to control the applied transducer contact pressure. For example, when the measured compression reaches the desired value determined in act 12, the increase in contact pressure of act 18 ceases. Alternatively, a reduction in pressure is controlled. As another example, the rate of increase is controlled in response to the difference between the desired value and the body tissue compression.

The control is a function of the desired value. The measured compression is of a same type of parameter as the desired value, or the desired value and/or the measured compression are converted to be the same type of parameter. For example, the desired value is an amount of elasticity. The elasticity of the tissue under the compression is measured. As another example, the desired value is a flow velocity. The measured compression is also a flow velocity. In another example, the desired value is a pressure. The measured compression is a change vessel diameter. The change in vessel diameter is mapped or modeled to a pressure. In yet another example, the desired value is the existence or not of acoustic reflection from a tissue layer. The measured compression is whether or not there is a tissue layer represented in the scan data.

The measured compression is compared to the desired value. The comparison may be direct, such as calculating a difference. In other embodiments, the comparison is part of a function accounting for other factors. For example, the comparison includes determination of a rate of change as well as an absolute value.

The control is automated or a user feedback. For example, a robotic support arm is locked in place or frozen when the desired compression is achieved. The robotic support arm may be controlled to move, not move, increase rate, decrease rate or other control of motors or arm movement. Motor control and/or braking may be used to stop increasing the pressure which may result in maintaining a substantially same pressure (although insubstantial variations may result from mechanical and/or other sources of give or tolerance). The pressure may be decreased slightly once the threshold is reached, such as setting the threshold at a level associated with over pressure for detection. After slight decrease, the pressure is maintained.

For controlling by user feedback, an audio, visual, and/or tactile (e.g., vibration) indication is output to the user. The user is instructed or warned to cease increasing pressure. The user may be instructed the rate at which the pressure is to be increased, such as with a bar or graph including feedback on the current increase. Once the desired pressure occurs, the user ceases increasing in response to the indication. The user and/or the robotic support arm may hold the transducer in place at the desired pressure.

The increase in pressure is halted when the measured compression or a derivative thereof reaches the desired value. In alternative embodiments, the desired pressure and compression vary over time so the feedback continues. As the pressure varies, feedback is provided to alter the pressure back to or closer to the desired level. Alternatively, the desired level varies over time so acts 16-20 continue to occur, allowing adjustment of the pressure and resulting compression. The increase of act 18 may be a decrease.

In act 24, the patient is scanned with the ultrasound transducer. This scanning occurs with the transducer being maintained or set at the desired pressure. While the pressure is maintained at about the desired level, the region of interest is acoustically scanned. The same or different type of scanning occurs in act 24 as performed in act 16. Act 16 is performed to provide compression measurement. Act 24 is performed to acquire data for diagnosis. The data for diagnosis may also be used for measuring compression, such as to maintain or confirm maintenance of the compression. The data for measuring the compression may also be used for diagnosis, such as providing one or more two-dimensional images for viewing and/or to determine elasticity of the tissue.

In one embodiment, the scanning of act 24 is a volume scan. For example, a three-dimensional scan of the breast is performed while maintaining the pressure. The three-dimensional region is scanned electronically or mechanically. For example, a one-dimensional array scans one portion for measuring compression. The array is then mechanically moved to scan different planar regions once the desired pressure is reached. The extent of the motion of the transducer may be greater due to sufficient acoustic coupling caused by the pressure. The "stick-slip" may be reduced since too much pressure may be avoided. The result is scan data representing the patient with fewer artifacts.

Figure 3:
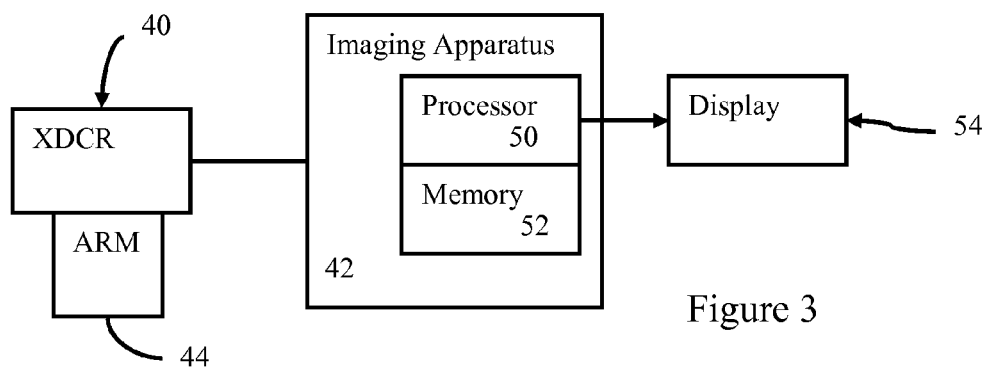
FIG. 3 is a block diagram of one embodiment of a system for controlling pressure in medical diagnostic ultrasound imaging.

FIG. 3 shows one embodiment of a system for controlling pressure in medical diagnostic ultrasound imaging. The system implements the method of FIG. 1 or other methods. The system includes the arrangement of FIG. 2, but may be free of the support arm 44. The system includes a transducer 40, an imaging system 42, a support arm 44, a processor 50, a memory 52, and a display 54. Additional, different or fewer components may be provided. For example, a speaker or tactile output device is provided for control of the increase in pressure by providing user feedback. As another example, the support arm 44 is not provided. In yet another example, the display 54 is not provided.

The transducer 40 is a single element transducer, a linear array, a curved linear array, a phased array, a 1.5 dimensional array, a two-dimensional array, a radial array, an annular array, a multidimensional array, a wobbler, or other now known or later developed array of elements. The elements are piezoelectric or capacitive materials or structures. In one embodiment, the transducer 40 is adapted for use external to the patient, such as including a hand held housing or a housing for mounting to an external structure. More than one array may be provided, such as a support arm holding two or more (e.g., four) wobbler transducers adjacent to a patient (e.g., adjacent an abdomen of a pregnant female). The wobblers mechanically and electrically scan and are synchronized to scan the entire fetus and form a composite volume. In other embodiments, a single hand-held or support held transducer is provided for scanning different planes after being moved to different positions. In alternative embodiments, the transducer 40 is adapted for use within the patient, such as being on a transesophegeal or cardiac catheter probe.

The transducer 40 converts between electrical signals and acoustic energy for scanning a region of the patient body. The region of the body scanned is a function of the type of transducer array and position of the transducer 40 relative to the patient. For example, a linear transducer array may scan a rectangular or square, planar region of the body. As another example, a curved linear array may scan a pie shaped region of the body. Scans conforming to other geometrical regions or shapes within the body may be used, such as Vector® scans. The scans are of a two-dimensional plane or a line. Different planes may be scanned by moving the transducer 40, such as by rotation, rocking, and/or translation. A volume is scanned. The volume is scanned by electronic steering alone (e.g., volume scan with a two-dimensional array), or mechanical and electrical steering (e.g., a wobbler array or movement of an array for planar scanning to scan different planes).

The support arm 44 releasably or fixedly holds the transducer 40. The support arm 44 moves with any number of degrees of freedom, such as one to seven degrees of freedom. In one embodiment, the support arm 44 includes shocks, springs or other mechanisms for making the support arm neutral—countering gravity. No actuators are provided. In other embodiments, actuators are provided. The support arm 44 may include one or more links and actuators for moving joints and/or providing assist to the user for moving the transducer 40. In one embodiment, one or more of the links are formed from a non-rigid flexible material, such as hard rubber. The non-rigid flexible material may assist in avoiding undo or over pressure on a patient. The non-rigid or a rigid link may be formed to break or bend in response to a threshold amount of pressure greater than the threshold pressure to be applied for the desired compression. The links connect at joints. The joints are rotatable, bendable, twistable or otherwise moveable around an axis or away from an axis of one of the links. Each joint may have one or more degrees of freedom. The actuators are electromagnetic, pneumatic, hydraulic or combinations thereof. The actuators move the support arm 44 in at least one, two or more degrees-of-freedom. For example, the actuators move one link relative to another link by rotation, flexing, bending or other motion.

The support arm 44 may include one or more sensors, such as position, force, pressure, displacement, or other types of sensors. In one embodiment, a position sensor connects to the transducer 40, the support arm 44 or both the transducer 40 and the support arm 44 for registering relative location of different scans. A force sensor may be adjacent or over an acoustic window of the transducer 40 or on the support arm 44 for sensing pressure applied to a patient. The pressure measurement from the support arm 44 may be used to determine a pressure applied to the patient. This pressure is measured independent of or to verify the measurements made using ultrasound data.

Another sensor may be another force sensor positioned on the transducer 40, the support arm 44 or both to sense user applied pressure. The sensor is positioned to determine an amount and/or direction of pressure applied by a sonographer. The support arm 44 may respond to sonographer-applied pressure to increase or decrease pressure applied to the patient or to assist in moving the support arm 44 with the actuators. In combination with the force sensor 16, the force applied to the patient by the sonographer and the support arm 44 is limited, but the force applied by the sonographer may be less than the force applied to the patient.

The support arm 44 with or without use of the sensors may be used for strain, elastography and/or palpation imaging. For example, the support arm 44 vibrates the transducer 40 at a controllable palpation frequency or using a palpation pulse. As another example, images associated with different amounts of pressure applied to the patient by the transducer 40 are acquired for strain or elastography determinations and/or for measuring compression.

The support arm 44 extends from a table, cart, wall, ceiling or other location. The base may be fixed or mounted, but alternatively is releasable or merely rests due to gravity on an object. The support arm 44 extends from the mount to the patient for scanning with the transducer 40.

The ultrasound imaging apparatus 42 is a medical diagnostic ultrasound system. For example, the ultrasound imaging apparatus 42 includes a transmit beamformer, a receive beamformer, a detector (e.g., B-mode and/or Doppler), a scan converter, and the display 24 or a different display. The ultrasound imaging apparatus 42 connects with the transducer 40, such as through a releasable connector. Transmit signals are generated and provided to the transducer 40. Responsive electrical signals are received from the transducer 40 and processed by the ultrasound imaging apparatus 42.

The ultrasound imaging apparatus 42 is configured by software and/or hardware to acquire ultrasound data representing a patient with the transducer 40. The ultrasound imaging apparatus 42 causes a scan of an internal region of a patient with the transducer 40 and generates data representing the region as a function of the scanning. The scanned region is adjacent to the transducer 40. For example, the transducer 40 is placed against a breast. The ultrasound data is beamformer channel data, beamformed data, detected data, scan converted data, and/or image data. The data represents anatomy of the region, such as the breast.

In another embodiment, the ultrasound imaging apparatus 42 is a workstation or computer for processing ultrasound data. Ultrasound data is acquired using an imaging system connected with the transducer 40 or using an integrated transducer 40 and imaging system. The data at any level of processing (e.g., radio frequency data (e.g., I/Q data), beamformed data, detected data, and/or scan converted data) is output or stored. For example, the data is output to a data archival system or output on a network to an adjacent or remote workstation. The ultrasound imaging apparatus 42 processes the data further for analysis, diagnosis, and/or display.

The processor 50 is a control processor, general processor, digital signal processor, application specific integrated circuit, field programmable gate array, network, server, group of processors, data path, combinations thereof or other now known or later developed device for controlling pressure using ultrasound feedback. For example, the processor 50 or a data path of processors including the processor 50 is configured to measure body tissue compression and control increase in the transducer contact pressure. As another example, the processor 50 or a data path including the processor 50 performs any combination of one or more of the acts shown in FIG. 1.

The processor 50 operates pursuant to instructions stored in the memory 52 or another memory. The processor 50 is programmed for determining an amount of contact pressure applied by the transducer against a patient. The contact pressure is determined from ultrasound data. The processor 50 determines when the amount of contact pressure is sufficient. The processor 50 indicates to the user when the amount is sufficient. Alternatively or additionally, the processor locks the support arm 44 when the amount of contact pressure is sufficient. The locking is performed by activating a brake and/or by restricting further operation of actuators. The locking or indication is a control to maintain a desired contact pressure during further scanning, such as during scanning for diagnostic information.

The memory 52 is a non-transitory computer readable storage media. The instructions for implementing the processes, methods and/or techniques discussed above are provided on the computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The memory 62 may store alternatively or additionally ultrasound data for measuring compression or for diagnosis. The ultrasound data is the radio frequency data, elasticity data, B-mode data, or other data, but may include alternatively or additionally data at different stages of processing.

The display 54 is a CRT, LCD, projector, plasma, or other display for displaying two-dimensional images, or three or four-dimensional renderings.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for controlling transducer contact pressure in medical diagnostic ultrasound imaging, the method comprising:
    placing an ultrasound transducer against a patient's breast;
    adjusting the amount of contact pressure applied by the ultrasound transducer against the breast;
    ultrasonically scanning, with the ultrasound transducer, a scan region of the breast, the scan region including a diagnosis region of interest and a near field region outside of the diagnosis region of interest;
    measuring, with ultrasound data received by the transducer due to the scanning, compression of body tissue caused by the pressure, the compression measured as a thickness of a skin layer or whether the skin layer is detectable, the skin layer being between the ultrasound transducer and the diagnosis region of interest, the skin layer in the near field region of interest and outside the diagnosis region of interest; and
    controlling the transducer contact pressure as a function of the measured compression of the body tissue.

2. The method of claim 1 wherein placing comprises positioning a robotic support arm connected with the ultrasound transducer, the robotic support arm operable to maintain the pressure against the breast applied by the ultrasound transducer.

3. The method of claim 1 wherein adjusting the amount of contact pressure comprises adding force by the user.

4. The method of claim 1 wherein ultrasonically scanning comprises scanning a planar region of the breast, the planar region extending from the ultrasound transducer into the breast and comprises repeating the scanning of the planar region during the adjusting.

5. The method of claim 1 wherein measuring the compression comprises measuring tissue deformation.

6. The method of claim 5 wherein measuring tissue deformation comprises correlating speckle from frames of ultrasound data obtained by the scanning at different times.

7. The method of claim 1 wherein measuring the compression further comprises measuring the compression in the diagnosis region of interest of the breast.

8. The method of claim 1 wherein controlling comprises comparing the measured compression to a threshold and ceasing the adjusting when the measured compression reaches the threshold.

9. The method of claim 8 wherein the threshold is adaptively determined based on a physiological characteristic of the patient.

10. The method of claim 9 wherein the physiological characteristic is an input age, height, weight, cup size, body mass index, or combinations thereof.

11. The method of claim 1 wherein controlling comprises ceasing the adjusting with the amount of the pressure at a first level;
    further comprising:
    maintaining the first level of the pressure; and
    performing a three-dimensional scan of the breast while performing the maintaining.

12. In a non-transitory computer readable storage medium having stored therein data representing instructions executable by a programmed processor for controlling transducer contact pressure in medical diagnostic ultrasound imaging, the storage medium comprising instructions for:
    measuring compression, at a skin layer outside a diagnosis region of interest, caused by an ultrasound transducer with ultrasound data from an ultrasound scan of a scan region, the compression measured as a thickness of a skin layer or whether the skin layer is detectable, the skin layer being in a near field of the scan region and outside the diagnosis region of interest;
    regulating an amount of pressure applied by the transducer as a function of the compression; and
    scanning, in addition to the ultrasound scan, the diagnosis region of interest with the ultrasound transducer with the amount of pressure regulated.

13. The non-transitory computer readable storage medium of claim 12 wherein measuring comprises determining tissue deformation caused by the pressure.

14. The non-transitory computer readable storage medium of claim 12 wherein measuring further comprises determining flow variation caused by change of the pressure.

15. The non-transitory computer readable storage medium of claim 12 wherein regulating comprises outputting an indication when the amount of the pressure reaches a threshold level and locking a robotic arm in place, the robotic arm holding the ultrasound transducer.

16. The non-transitory computer readable storage medium of claim 12 wherein scanning comprises scanning a three-dimensional region as the scan region while the pressure is maintained at about a threshold level.

17. A system for determining contact force in medical diagnostic ultrasound imaging, the system comprising:
    a transducer;
    a support arm operable to hold the transducer;
    an ultrasound imaging apparatus connected with the transducer, the ultrasound imaging apparatus configured to acquire, with the transducer, ultrasound data for a scan region including a diagnosis region of interest and a near field region outside of the diagnosis region of interest representing a patient; and
    a processor configured to determine an amount of the contact force applied by the transducer against a patient, the processor determining the amount of contact force from a thickness of a skin layer or whether the skin layer is detectable, the skin layer being between the transducer and the diagnosis region of interest, the skin layer in the near field region of interest and outside the diagnosis region of interest, from the ultrasound data representing the skin layer, the processor configured to determine when the amount is sufficient.

18. The system of claim 17 wherein the processor is configured to lock the support arm when the amount is sufficient such that the sufficient amount is maintained during further scanning.

* * * * *